United States Patent
Filser et al.

(10) Patent No.: US 7,537,449 B2
(45) Date of Patent: *May 26, 2009

(54) HOLDING DEVICE FOR A DENTURE OR BASE STRUCTURE MODEL

(75) Inventors: Frank Filser, Oberengstringen (CH); Ludwig Gauckler, Schaffhausen (CH); Peter Kocher, Wallisellen (CH); Heinz Luethy, Neuchâtel (CH); Peter Schaerer, Zurich (CH); Heiner Hoerhold, Budingen (DE); Peter Kreuder, Bad Nauheim (DE); Stefan Fecher, Johannesberg (DE)

(73) Assignee: Eidgenossiche Technische Hochschule Zurich Nichtmetallische Werkstoffe, Zurich (CH)

( * ) Notice: Subject to any disclaimer, the term of this patent is extended or adjusted under 35 U.S.C. 154(b) by 207 days.

This patent is subject to a terminal disclaimer.

(21) Appl. No.: 11/391,872

(22) Filed: Mar. 28, 2006

(65) Prior Publication Data
US 2006/0194165 A1    Aug. 31, 2006

Related U.S. Application Data

(63) Continuation of application No. 10/433,876, filed on Jun. 3, 2003, now Pat. No. 7,101,180.

(51) Int. Cl.
    *A61C 1/14* (2006.01)
(52) U.S. Cl. .......................... 433/49; 269/53
(58) Field of Classification Search .............. 433/25, 433/34, 49, 60, 55–56, 74, 153–154, 163; 269/53
    See application file for complete search history.

(56) References Cited

U.S. PATENT DOCUMENTS

| | | | | | |
|---|---|---|---|---|---|
| 1,271,161 | A | * | 7/1918 | Hall | 433/59 |
| 2,627,113 | A | * | 2/1953 | Moray | 433/154 |
| 2,682,109 | A | * | 6/1954 | Roux, Jr. | 433/154 |
| 3,060,579 | A | * | 10/1962 | Sharp | 433/154 |
| 3,068,572 | A | * | 12/1962 | Gobby | 433/49 |
| 4,128,942 | A | * | 12/1978 | Schleich | 433/60 |
| 4,319,875 | A | * | 3/1982 | Beckwith | 433/60 |
| 5,482,460 | A | * | 1/1996 | Farnor et al. | 433/57 |
| 5,716,209 | A | * | 2/1998 | Faierstain | 433/60 |

* cited by examiner

*Primary Examiner*—John J Wilson
(74) *Attorney, Agent, or Firm*—Bachman & LaPointe, P.C.

(57) ABSTRACT

A holding device that can be braced in a surveying machining together with an individual preparation model produced by dental laboratory techniques. The holding device has a mechanically stable frame with bores disposed at a distance (a) to one another, in which at least two holding pins are locked that can be displaced at least in the axial direction (A).

10 Claims, 4 Drawing Sheets

HOLDING DEVICE FOR A DENTURE OR BASE STRUCTURE MODEL

CROSS REFERENCE TO RELATED APPLICATION

This application is a continuation application of application Ser. No. 10/433,876 which was filed on Jun. 3, 2003, now U.S. Pat. No. 7,101,180 entitled HOLDING DEVICE FOR A DENTURE OR BASE STRUCTURE MODEL.

BACKGROUND OF THE INVENTION

The invention relates to a holding device comprising an individual tooth replacement or basic framework model produced by dental technology and means for clamping the device in a measuring machine. The invention also relates to a method for positioning a model of this type in a holding device.

Tooth replacement or basic framework models, hereinafter called preparation models, have different shapes and sizes. They consist primarily of modelling wax or modelling plastics material. It is necessary to measure them to work the tooth replacement or the basic framework for tooth restorations from an industrially preproduced blank with the aid of manual, semi-automatic or automatic production apparatus. Tooth restorations are, for example, tooth crowns and bridges comprising a load-bearing basic framework on which further layers made of porcelain, ceramic or plastics material are applied. Basic frameworks are individual productions and are usually produced once individually for a patient in the normal procedure. It is similar for a tooth replacement which, apart from the basic framework, already contains layers made of porcelain, ceramic or plastics material.

Preparation models which are produced individually for a patient vary with respect to length, width and positioning of the individual parts. They can be differently bent both in the cranio-caudal and bucco-palatinal direction according to the anatomical conditions. Basic frameworks consist of a small cap for tooth crowns. These have an inside and an outside, which may be completely or partially coated, forming the cavity. The inside of the cavity fits precisely on the natural tooth prepared by the dentist, the tooth stump or else on an artificial tooth stump, for example an implant. Tooth bridges consist of a plurality of connected members of which at least one is designed as a small cap, while the others can be designed as bridge and/or exstress members. Cavities per se have to be free of undercuts in alignment to the other cavities, so the tooth restoration can be placed as a whole onto the prepared teeth.

Measuring a preparation model offers an important advantage compared to measuring a plaster model, in that the dental technician can design and assess the physical model as previously with his familiar aids. With objects shaped as complexly as this, visual and touch impressions are very important. Supplementing the measuring data on the computer does not offer the dental technician the same familiar impressions and is therefore much more challenging to his powers of abstraction and imagination. Producing preparation models from wax, plastics material or other easily processible materials is known in dental technology as general expert knowledge and guide to handling and therefore prior art. This technology is also used, in particular for moulding methods, for example in the widespread casting and hot press technology. Measuring such preparation models requires them to be fixed in a measuring machine, preferably on its rotary shaft.

Preparation models, in other words in particular models for basic frameworks for tooth crowns and bridges, are already frequently used in dental technology. They are formed by the casting method and hot press method, for example a negative mould of the basic frame being developed in a fireproof mould. The negative mould represents a cavity which is then filled with dental material. These methods are not considered here.

Other methods measure the preparation model digitally, or they transfer the mould of the preparation model during measurements, by means of mechanical coupling, to the machining tools. All methods of this type need a suitable holding device for the preparation model.

DE, C1 19916148 describes a universal holder for holding operating means, inter alia models in tooth technology. Owing to the combination of rigid and formable parts in the holder any adjustment angles can be achieved. The formable part is designed like a cushion and has a reversibly formable outer skin, which is filled with granules. This allows a spatial, single-handed orientation of workpieces during machining, in particular during casting of dental impressions and dental technology models.

An automatic machine tool for measuring preparation models and producing basic frameworks, in particular for tooth crowns and/or tooth bridges of precise three-dimensional design, is described in PCT/CH00/00623. This machine tool comprises a machine frame or a machine housing, with a rotary shaft for a support for the blank on one side and a support for the preparation model on the other side, at least one machining unit, at least one measuring or digitalising unit and an electronic computing and control unit for all the drive members. A movement unit with three axes of translation in the x, y and z directions is formed for machining unit(s) and measuring unit(s). The digitalisation of the preparation model and machining of the blank are carried out on the same machine tool, at different times. Prior to machining the blank the machining paths for the blank are calculated from the determined and stored digitalisation data, a preset, material-specific scale factor and the tool geometry.

With a view to the prior art it can be established that no convincing specific holding device for dental preparation models is known; there are merely rudimentary aid solutions.

The object of the present invention is [therefore] to provide a holding device of the type mentioned at the outset, in which the individuality of the preparation model and its complex form is particularly taken into account. The preparation model must be fixable free of undercuts. Moreover, a method for positioning a preparation model in its holding device is to be provided.

SUMMARY OF THE INVENTION

The object is achieved according to the invention in that a holding device comprises a mechanically stable frame with holes arranged at a spacing, in which at least two holding pins which can be displaced in the axial direction are locked, the holding pins being connected on the end face by means of a bonding agent to the preparation model which is aligned free of undercuts in relation to a defined position, and fixing it rigidly and without stress to the frame, and the equipped frame can be clamped into the measuring machine in a manner secured against slipping and rotation by a clamping adapter on the machine side.

The position and number of the holding pins are established owing to the experiences of the person skilled in the art and/or calculations for optimisation. These depend in particular on the form and size of the preparation model. The above-mentioned position with respect to the preparation model is defined by the clamping adapter and, for example, a flattening.

Experiences and/or calculations also advantageously take into consideration that the position and dimensioning of the holding webs of the workpiece which is worked from the blank later or simultaneously, is established by also measuring the holding pins. This blank must be held securely during machining.

The frame used according to the invention can be designed in different shapes, widths, lengths and cross-sectional shapes. This frame may also be closed or U-shaped in design, the two sides preferably extending over the entire length of the preparation model.

The frame suitably consists of a metal, for example aluminium or an aluminium alloy, or a mechanically rigid plastics material, for example a Macrolon. The holding pins for the preparation model may consist of the same material, or else of a mechanically rigid plastics material.

In the case of a rigid frame designed to be square or rectangular, the holes are preferably arranged distributed over the entire frame, generally with regular spacing. At points which are important for holding the preparation model, a plurality of holes may also be recessed.

The longitudinal axes of the holes extend basically on the centre plane of the frame, in each case suitably perpendicularly to the inner plane of the relevant frame part. Obviously, the longitudinal axes of the holes could also be located individually or in groups outside the mentioned plane and/or otherwise be arranged obliquely.

It is of essential importance that the holding pins can be freely displaced along their longitudinal axis, so the distance between the frame and the preparation model is optimally bridged.

A pivotable cylinder, preferably with a longitudinal axis extending parallel or perpendicular to the frame, or a ball-and-socket head, can be installed in the frame at one or more positions, with at least one positionable holding pin, in each case.

For more complicated preparation models, it is advantageous if the frame is designed at least partially in two parts, with at least one fixed guide rail designed for example so as to be cross-sectionally dovetail-shaped, I-shaped or T-shaped and at least one lockable slide sliding thereon, having at least one hole for a holding pin. In this way the positioning of the holes along the frame need not only be at specific positions, but may be continuously adjustable.

According to a further development a pivotable cylinder can be formed in a slide formed as above, preferably with a longitudinal axis extending parallel or perpendicular to the frame.

At least one rotatable and longitudinally displaceable hollow cylindrical slide with at least one hole can also be arranged on a cylindrical fixed guide rail. A further degree of freedom is therefore obtained; the holding pins cannot only be displaced in one direction of the frame, but can also be pivoted perpendicular thereto.

Finally, according to a third variation, at least one ball-and-socket joint head can be mounted in one or more slides, so the holding pins cannot only be displaced longitudinally but are also pivotable in any direction.

Both the slides and also the pivoting cylinder and ball-and-socket joint head can be locked in any position by means which are known per se, in particular with a fixing screw.

With respect to the method for positioning a preparation model in a holding device, the object is achieved according to the invention in that the frame and the preparation model are fixed outside the measuring machine, the number and position of the holding pins is established, the pins are guided into the relevant hole and with the bonding agent applied to the end face, placed on the surface of the preparation model and all the holding pins and their holders are fixed in the frame. The equipped holding device is uncovered once the bonding agent has cured. The holding device can then be clamped in a predefined position in the measuring machine.

It is of essential significance to the invention that the holding pins are not pressed on the surface of the preparation model, but are placed without the exertion of pressure so no stresses develop.

Particularly simple and therefore advantageous fixing of the holding pins takes place by stippling some wax or adhesive onto the relevant part of the frame. Moreover, all fixing screws and similar fastening means are tightened.

As already mentioned, the preparation model together with the holding pins is measured. Firstly, one side of the preparation model is measured, then the holding device clamped to the rotary shaft of a measuring machine is turned and the second side of the preparation model is measured or digitalised.

The holding device according to the invention has a plurality of advantages:

The individuality of preparation models is completely taken into account by the possibility of variation in the holding positions.

The alignment of the preparation model, free of undercuts, may take place outside the measuring machine and is therefore not impeded by limited possibilities for viewing and moving.

The holding device can be reused after the development of the preparation model.

BRIEF DESCRIPTION OF THE DRAWINGS

The invention will be described in more detail with the aid of embodiments shown in the drawing, which are also the subject of dependent claims. The drawings show schematically:

DETAILED DESCRIPTION

Figure 1:
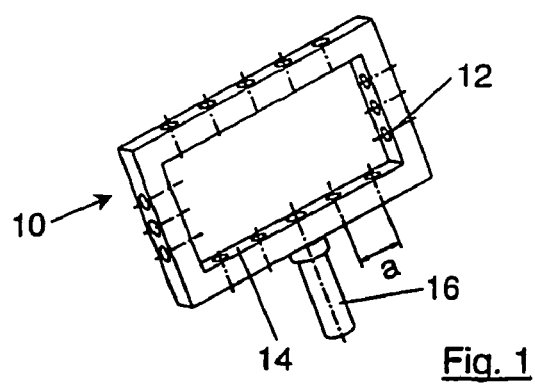
FIG. 1 a perspective view of a closed frame,
FIG. 2 a view of an open frame,
FIG. 3 a view of a closed frame with a preparation model,
FIG. 4 a lateral view of FIG. 3 in cross-section,
FIG. 5 a cut-open view of a holding pin inserted in a frame,
FIG. 6 a variation of FIG. 5,
FIG. 7 a further variation according to FIG. 5, in a sectional plan view,
FIG. 8 a section through a frame with a ball-and-socket joint,
FIG. 9 a section through a two-part frame,
FIG. 10 a view according to FIG. 9,
FIG. 11 a section through a variation of a two-part frame,
FIG. 12 a part section along the longitudinal centre plane of a frame,
FIG. 13 a section according to XIII-XIII in FIG. 12,
FIG. 14 a variation according to FIG. 12, and
FIG. 15 a section according to XV-XV in FIG. 14.

FIG. 1 shows a closed frame 10 of a holding device according to the invention. The frame 10 consists of an aluminium alloy and is mechanically stable. Holes 12 for holding pins, which are not shown in FIG. 1, are provided over the entire periphery of the frame 10 having a rectangular basic form, at a regular spacing a. The holes 12 extend perpendicular to the inner face 14 of the frame 10, the longitudinal axes A of the holes are provided on the centre plane of the frame. A clamping adapter 16 is flanged on the machine side in the centre of a longitudinal side of the frame. This clamping adapter 16 is fastened in a specific position so as to be secure against slipping and rotation on the rotary shaft of a measuring machine, not shown. According to one variation, the clamping adapter 16 is flanged on the centre of the narrow side of the frame 10.

Figure 2:
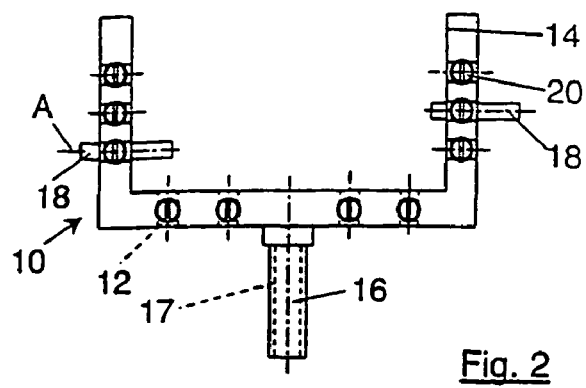

FIG. 2 shows an open, substantially U-shaped frame 10. The two sides of the frame 10 are approximately of the same length as the narrow sides of a closed frame. In the holes 12 of the frame shown by dashed lines two holding pins are inserted to different depths and each is fastened with a fixing screw 20. Because of the low effective forces, the frame does not have to be very rigid in design. The open frame 10 according to FIG. 2 provides improved accessibility and also the possibility of receiving very bent preparation models. At most, the positioning of the holding pins 18 is slightly limited relative to a closed frame 10. A rotation prevention device 17 is provided on the clamping adapter 16 and is designed in the form of a flattening or a bolt and thus represents a predetermined indicator for the position of the holding device free of undercuts.

Figure 3:
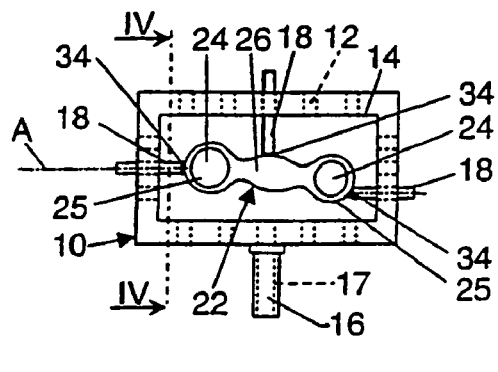
Figure 4:
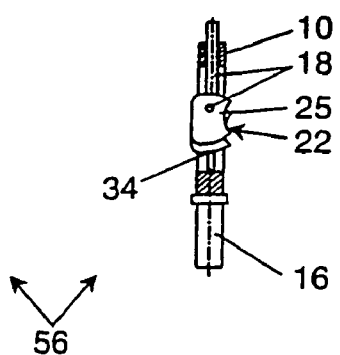

FIG. 3 shows an individually produced three-membered preparation model 22 made of wax, in the present case a basic framework model, which is fastened with three cylindrical holding pins 18 in a rectangular frame 10 of the holding device 56. The frame consists in the present case of plastics material, is 50 mm in length and 30 mm in width and has a rectangular recess of 42 mm in length and 22 mm in width. The cross-section of the frame is rectangular having a height of 6 mm and a width of 4 mm. Five through-holes 12 are formed on the narrow side of the frame 10, six holes 12 on the longitudinal side of the clamping adapter 16, and seven holes 12 on the opposing longitudinal side. The holes each have a diameter of 1.25 mm. Three straight cylindrical holding pins made of plastics material with a diameter of 1.2 mm are pushed through three predetermined holes 12. The preparation model 22 is initially aligned free of undercuts, so a milling tool could potentially machine the surface from one direction, its machining direction. The preparation model 22 is preferably aligned with the cavities 24, as this part of the surface represents the most difficult and quality-determining part. The preparation model 22 is held precisely in this aligned position and the frame 10 is placed with the holding pins 18 with the recess over the preparation model 22. The holding pins 18 are carefully pushed along their axial direction A until they contact the preparation model 22 with the bonding agent 34 (wax) applied to the end face, and therefore waxed on.

The holding pins 18 are mesially and distally connected to the outside of the two small caps 25 and lingually to the bridge member 26. The holding pins 18 are fixed to the frame 10 by fixing screws 20, not shown.

This equipped frame with the holding pins 18 and the inserted preparation model 22 is inserted in a measuring machine in a manner secured against slipping and rotation by means of the clamping adapter 16 on the machine side. The clamping adapter 16 preferably has a marking, for example a flattening or a transverse pin, so that it adopts a predetermined position in the measuring machine.

After clamping, the preparation model 22 can initially be measured on one side then on the other side. The holding pins 18 are measured together with the preparation model 22 and serve to reliably receive the machining forces during the later material removal from a blank. The holding forces are small during measuring, predominantly acceleration forces, gravitational forces and at most the pressure force of tactile measuring occur. After measuring, the frame 10 with the preparation model 22 is taken from the measuring machine, the fixing screws 20 are released and the holding pins 18 detached by turning from the preparation model 22. The frame 10 and the holding pins 18 are reusable, regardless of whether they consist of metal and/or plastics material.

During insertion, as mentioned, a bonding agent 34 is applied to the end faces of the holding pins 18, generally a wax or a thermoplastic adhesive, which fixes the holding pin 18 when applied to the preparation model 22. Even if the pins 18 are already inserted in the through-holes 12, the bonding agent 34 can subsequently be applied to the holding pins 18 shortly before contact with the preparation model 22.

The holding pins 18 protruding outwardly from the frame 10 are preferably severed flush with the surface.

Figure 5:
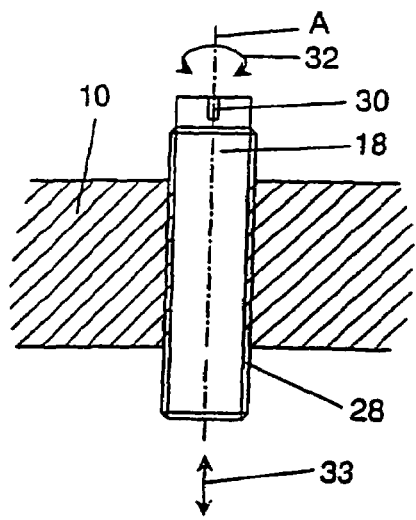

According to the embodiment of FIG. 5 a hole 12 is formed with an internal screw thread. A holding pin 18 provided with an external thread 28 is screwed therein. A diagonal slot 30 allows the turning of the holding pin 18 with a screwdriver, indicated by a double arrow 32. A second double arrow 33 indicates the axial movement directions of the holding pin 18.

Figure 6:
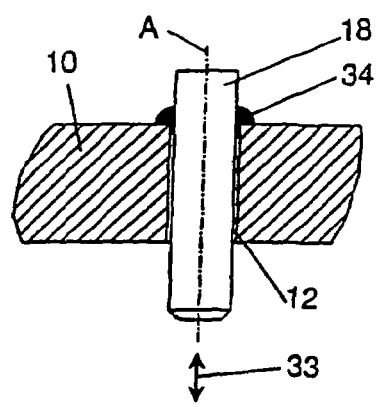

According to the variation of FIG. 6, a holding pin 18 is inserted with play (loose fit) into a hole 12 in the frame 10. It can be freely displaced in the axial direction A and this is indicated by the double arrow 33. Fixing takes place by means of a bonding agent 34, a wax or an adhesive, which partially penetrates into the gap between the frame and holding pin and thus ensures good fixing.

Figure 7:
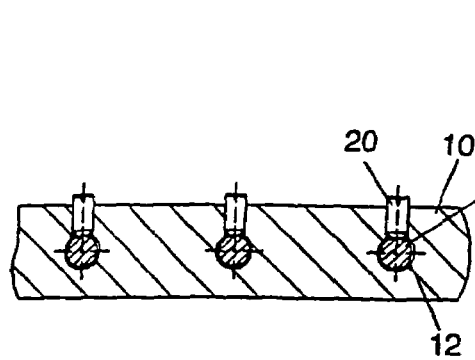

In FIG. 7 the direction of viewing is in the longitudinal direction of the holding pins 18, also inserted loosely into holes 12 in the frame 10. The holding pins 18 are here fixed by fixing screws 20.

All the fixing possibilities can be freely combined. The property that the holding pins 18 can be pushed onto the preparation model 22 (FIG. 3) by displacement in their axial direction A, can be placed there and then fixed in the frame, is important.

Figure 8:
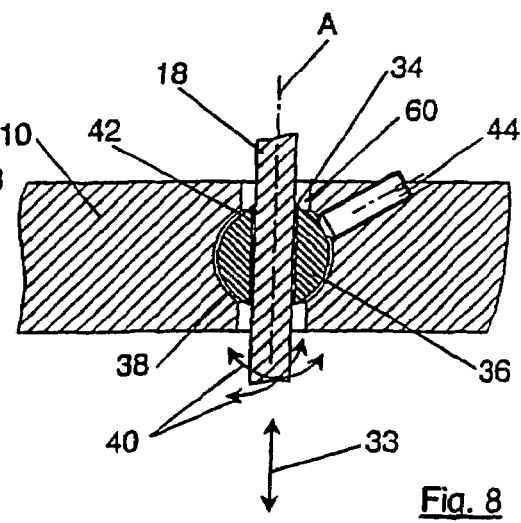

According to a further variation according to FIG. 8, a holding pin 18 can be mounted by means of a ball-and-socket joint head 36 in a corresponding joint socket 38 of the frame 10. The holding pin 18 can be inserted in the axial direction A during fastening of the preparation model 22 (FIG. 3) and because of the capacity of the ball-and-socket joint 36 to rotate can be pivoted in two directions which are linearly independent of one another, which is indicated by two crossed double arrows 40. Once the bonding agent 34 has cured on the surface of the preparation model 22 (FIG. 3) the holding pin 18 with the bonding agent 34 is fixed in the central hole 42 of the ball-and-socket joint head 36 and the ball-and-socket joint head 36 is then locked with a fixing screw 44. A recess 60 limits the pivoting region of the holding pin 18 in the direction of the double arrows 40.

Figure 9:
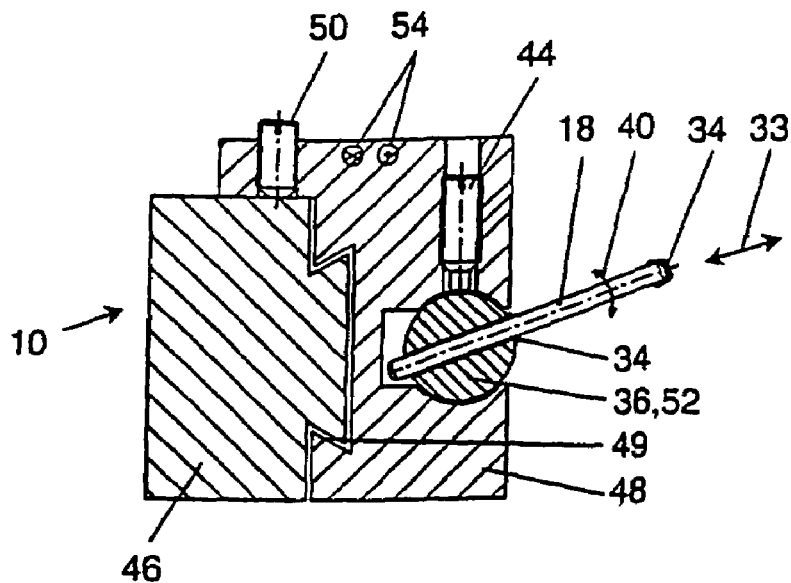

FIG. 9 shows a cross-section through a two-part frame 10. A slide 48 which is held by way of a dovetail guide 49 slides on a fixed guide rail 46. The slide 48 can be freely displaced along the dovetail guide 49 and can be locked in any position by a fixing screw 50. A ball-and-socket joint head 36 or a pivotable cylinder 52 is mounted in a corresponding recess of the slide 48. The holding pin 18 which can be axially displaced in the direction A of the double arrow 33 can thus be brought with its end face covered by a bonding agent 34 to any position in the frame. Displacement in the direction of the double arrow 33 is limited by the design. Once the bonding agent 34 has cured on the preparation model 22 (FIG. 3) locking takes place with a bonding agent 34 for the holding pin 18, a fixing screw 44 for the ball-and-socket joint head 36 or the pivotable cylinder 52 and the fixing screw 50 for the slide 48 which is displaceable in the direction of the double arrow 54.

Figure 10:
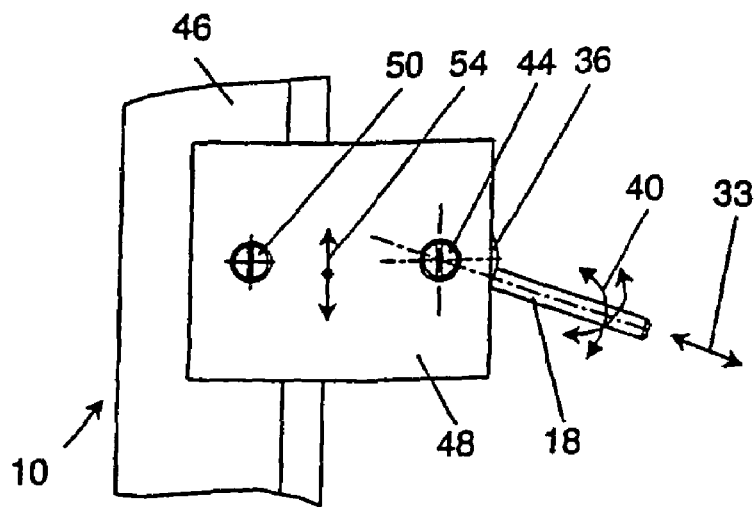

FIG. 10 shows the variation with the ball-and-socket joint 36 of FIG. 9 from another viewing direction.

Figure 11:
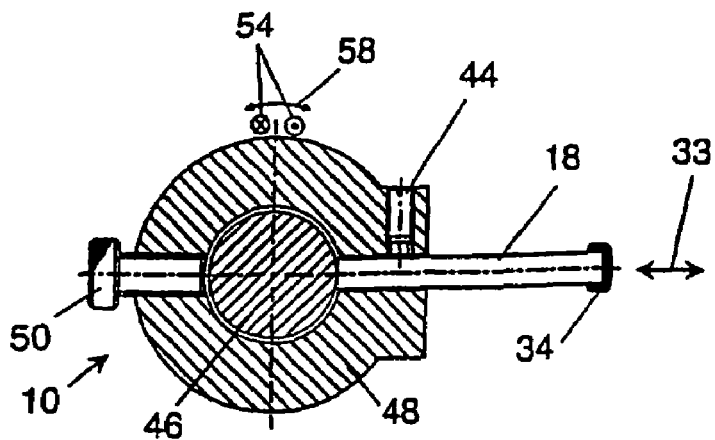

FIG. 11 shows a further embodiment with a fixed guide rail 46 with a cylindrical cross-section and a hollow cylindrical slide 48 which can be freely displaced and rotated thereon. Displacement of the slide 48 takes place in the direction of the double arrow 54, the rotation in the direction of the double arrow 58. The holding pins which are displaceable in the axial direction A in the direction of the double arrow 33 can thus with their end face find any point on the surface of the preparation model 22 (FIG. 3). Once the bonding agent 34 has cured on the surface of the preparation model 22, the fixing screws 44 and 50 are tightened and the holding pins 18 and the slide 48 are thus fixed.

Figure 12:
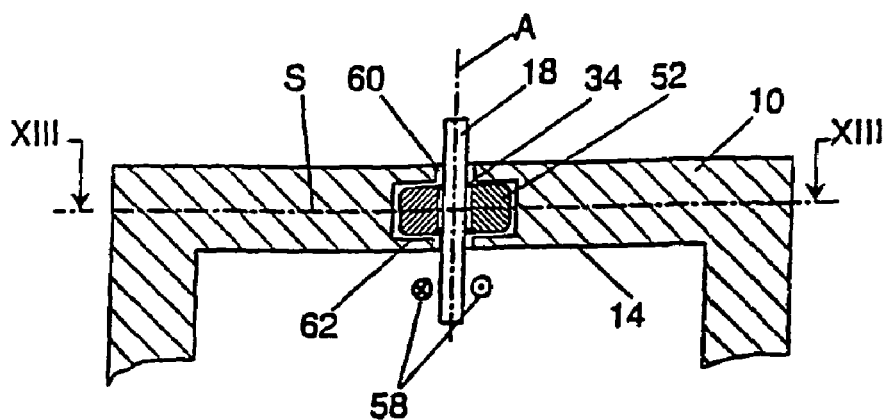
Figure 13:
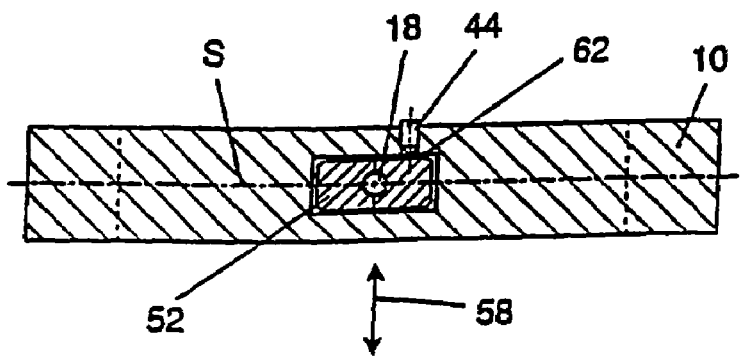

FIG. 12, 13 show a cylinder 52 mounted in the frame 10 with a pivoting axis S extending on the frame plane, the pivoting axis S also extending parallel to the relevant inner face 14. A holding pin 18 is longitudinally displaceably guided in the cylinder 52, which can be pivoted in the direction of the double arrow 58, and is fixed with a bonding agent 34. The pivoting movement in the direction of the double arrow 58 is limited by the dimensions of a recess 60 with a cylindrical roller bearing 62. The pivoting position of the cylinder 52 is limited by a fixing screw 44.

Figure 14:
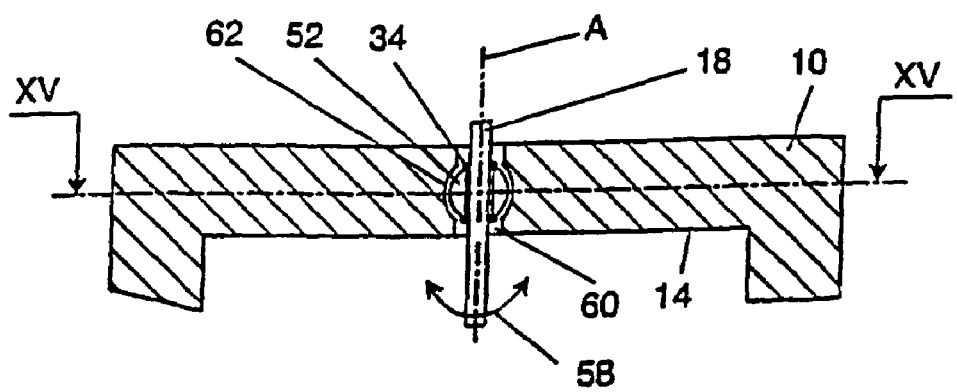
Figure 15:
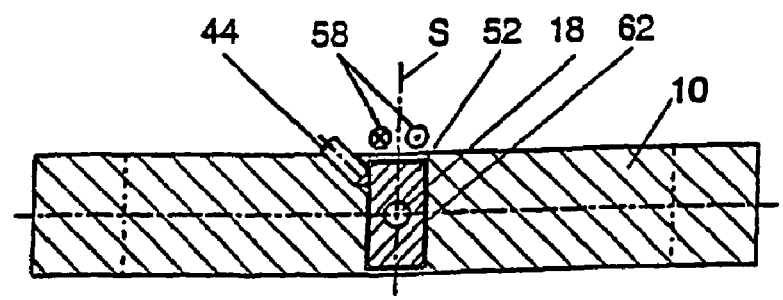

FIG. 14, 15 substantially correspond to the previous two figures. However, the axis S of the cylinder 52 extends perpendicularly to the frame plane and parallel to the relevant inner face 14.

It is obvious that more than one holding pin 18 per cylinder can also be arranged in all the embodiments according to FIG. 12 to 15.

The invention claimed is:

1. A holding device comprising holding an individual preparation model produced by dental technology, the individual preparation model consists of a basic framework model for tooth crowns and bridges and is made of one of modeling wax and modeling plastics material, secured in the holding device, the holding device comprises a frame having a plurality of sides, wherein each of the plurality of sides has at least one hole which together constitute a plurality of boles, a first holding pin located in a first hole and a second holding pin located in a second hole, the first and second holding pins each having an end face having a bonding agent for engaging the individual preparation model, means for locking the holding pins in engagement with the individual preparation model for holding the individual preparation model within the frame, whereas the holding pins are placed on the surface of the individual preparation model without the exertion of pressure, and the frame includes clamping means on external peripheral surface of the frame for fixing the holding device into a measuring machine.

2. A holding device according to claim 1, wherein the frame is designed to be one of closed and U-shaped with sides extending substantially over the dimensions of the preparation model.

3. A holding device according to claim 1, wherein the frame is one of square and rectangular.

4. A holding device according to claim 1, wherein the first and second holes extend in a plane which is perpendicular to an inner face surface of the frame.

5. A holding device according to claim 1, wherein a wax adhesive is applied on the end face as the bonding agent.

6. A holding device according to claim 1, wherein at least a part of the holding pins have an external thread and the corresponding holes have an internal thread.

7. A holding device according to claim 1, wherein the frame is designed in at least two parts, comprising a fixed guide rail and lockable slide, the slide having the holes for the holding pins.

8. A holding device according to claim 7, wherein the slide with holes for the holding pins is formed on cylindrically designed fixed guide rails.

9. A holding device according to claim 7, wherein the slide which is longitudinally displaceable on one of a dovetail-shaped, I-shaped, and T-shaped guided rail includes pivotable heads having holes for the holding pins.

10. A method for positioning a preparation model in a holding device comprising using the holding device of claim 1, and further comprising the steps of inserting the holding pins in the relevant hole and placed with the bonding agent applied to the end face of the preparation model, and locking all the holding pins so as to be secured against displacement and rotation against the preparation model.

* * * * *

UNITED STATES PATENT AND TRADEMARK OFFICE
CERTIFICATE OF CORRECTION

PATENT NO. : 7,537,449 B2
APPLICATION NO. : 11/391872
DATED : May 26, 2009
INVENTOR(S) : Frank Filser et al.

Page 1 of 1

It is certified that error appears in the above-identified patent and that said Letters Patent is hereby corrected as shown below:

In Column 7, claim 1, line 45, delete "boles," and insert --holes,--.

In Column 8, claim 1, line 9, delete "on external" and insert --on an external--.

Signed and Sealed this

Fifteenth Day of September, 2009

David J. Kappos
*Director of the United States Patent and Trademark Office*